US011535582B2

(12) United States Patent
López Fernández et al.

(10) Patent No.: US 11,535,582 B2
(45) Date of Patent: Dec. 27, 2022

(54) LEVULINIC ACID PURIFICATION

(71) Applicant: TÉCNICAS REUNIDAS, S.A., Madrid (ES)

(72) Inventors: Vicente López Fernández, Madrid (ES); Lourdes Arribas Martínez, Madrid (ES); Maria Frades Tapia, Madrid (ES); Álvaro Ruiz Pérez, Madrid (ES)

(73) Assignee: TÉCNICAS REUNIDAS, S.A., Madrid (ES)

( * ) Notice: Subject to any disclaimer, the term of this patent is extended or adjusted under 35 U.S.C. 154(b) by 0 days.

(21) Appl. No.: 17/260,645

(22) PCT Filed: Jul. 17, 2019

(86) PCT No.: PCT/EP2019/069230
§ 371 (c)(1),
(2) Date: Jan. 15, 2021

(87) PCT Pub. No.: WO2020/016290
PCT Pub. Date: Jan. 23, 2020

(65) Prior Publication Data
US 2021/0253508 A1    Aug. 19, 2021

(30) Foreign Application Priority Data
Jul. 18, 2018    (EP) .................................... 18382538

(51) Int. Cl.
*C07C 51/48*    (2006.01)
*C07C 51/47*    (2006.01)
*B01D 3/10*    (2006.01)
*B01D 11/04*    (2006.01)
*B01D 61/02*    (2006.01)
(Continued)

(52) U.S. Cl.
CPC ................ *C07C 51/48* (2013.01); *B01D 3/10* (2013.01); *B01D 11/0492* (2013.01); *B01D 61/02* (2013.01); *C07C 51/44* (2013.01); *C07C 51/47* (2013.01); *C07C 53/126* (2013.01)

(58) Field of Classification Search
CPC ......... C07C 51/48; C07C 51/44; C07C 51/47; C07C 53/126; B01D 3/10; B01D 61/02; B01D 11/0492
See application file for complete search history.

(56) References Cited

U.S. PATENT DOCUMENTS 6,054,611 A    4/2000   Farone et al.
2018/0297927 A1*  10/2018  De Rijke ................ C07C 51/43

FOREIGN PATENT DOCUMENTS

CN           101875605 A         5/2015
CN           107867996 A  *      4/2018  ............. C07C 51/47
WO    WO-2013034763 A1 *       3/2013  ............. B01D 3/145
(Continued)

OTHER PUBLICATIONS

CN 107867996, Song Qi, Separation method for levulinic acid compounds, 14 pages, English translation (Year: 2018).*
(Continued)

*Primary Examiner* — Yate' K Cutliff
(74) *Attorney, Agent, or Firm* — Gary J. Gershik

(57) ABSTRACT

The present invention refers to a process for the purification of levulinic acid, an aqueous solution comprising levulinic acid and a process for the production of levulinic acid.

19 Claims, 2 Drawing Sheets

(51) Int. Cl.
*C07C 51/44* (2006.01)
*C07C 53/126* (2006.01)

(56) References Cited

FOREIGN PATENT DOCUMENTS

| WO | WO 2014/037560 A1 | 3/2014 | | |
|----|-------------------|--------|----|----|
| WO | WO 2014/087016 A1 | 6/2014 | | |
| WO | WO 2015/007602 A1 | 1/2015 | | |
| WO | WO 2015/063033 A1 | 5/2015 | | |
| WO | WO-2017064069 A1 * | 4/2017 | ............. | C07C 51/43 |

OTHER PUBLICATIONS

Mulder, M et al., "Basic Principles of Membrane Technology", Kluwer Academic in Dordrecht, 1996 (Summary).
Schafer A.I. and Fane, A.G., "Chemical speciation effects in nanofiltration separation", Nanofiltration: Principles and Applications in edn., Original, Elsevier Advanced Technology, 2005 (Summary).

\* cited by examiner

LEVULINIC ACID PURIFICATION

RELATED APPLICATIONS

This application is a § 371 national stage of PCT International Application No. PCT/EP2019/069230, filed Jul. 17, 2019, claiming priority of European Patent Application No. 18382538.9, filed Jul. 18, 2018, the contents of each of which are hereby incorporated by reference into this application.

FIELD OF THE INVENTION

The present invention relates to the area of purification or extraction of levulinic acid. More specifically, the present invention relates to a process for the purification of levulinic acid, an aqueous solution comprising levulinic acid and a process for the production of levulinic acid.

BACKGROUND

Levulinic acid is a starting molecule for the synthesis of esters known as fuel additive and is known to be useful as a plasticizer and as a solvent. Moreover, levulinic acid can be used to synthesize methyl tetrahydrofuran (MTHF). Other applications of levulinic acid are for example the synthesis of delta-amino levulinic acid used as herbicide and pesticide, diphenolic acid used to synthesize polycarbonates and succinic acid used to make polyesters. Levulinic acid can also be used to produce gamma valerolactone (5-methylbutyrolactone), which in turn can be used for production of adipic acid (1,6-hexanedioic acid). Additionally, levulinic acid is an intermediate in the production of liquid fuels from biomass.

The production of levulinic acid from lignocellulosic biomass has been disclosed in numerous documents such as U.S. Pat. No. 6,054,611A, WO2014087016A1, WO2014037560A1, and WO2015007602A1.

Lignocellulose contains cellulosic-polymers bound together by lignin. When subjected to an acid treatment, lignocellulose splits into lignin and cellulosic components. These cellulosic components can then be hydrolyzed to their constituent pentose and hexose monomers. The pentose monomers, upon further acid treatment, can degrade to furfural, and the hexose monomers can degrade to hydroxymethylfurfural (HMF) which can further degrade in the presence of acid to levulinic acid (LEVA) and formic acid (FA).

Great purification and separation effort is needed in order to remove unwanted components and side products, as tar or humins, from the reaction mixture in order to obtain levulinic acid. For example, U.S. Pat. No. 6,054,611A discloses the purification of levulinic acid from an aqueous biomass hydrolysate by distillation followed by vacuum distillation and optionally, recrystallization. Also, several documents such as WO2014087016A1, WO2014037560A1 and WO2015007602A1 describe purification methods involving a solvent-extraction step that yields to an organic phase comprising levulinic acid that can be further purified. For example Patent Application No. WO2014087016A1 suggests recovering the levulinic acid and/or the formic acid from the organic phase by distillation. Patent Application No. WO2014037560A1 suggests subjecting said organic phase to nanofiltration, and optionally to a further distillation step. Also, Patent Application No. WO2015007602A1 describes a process for the isolation of levulinic acid from an organic solution that comprises a step of washing said organic solution with an alkaline aqueous stream to yield a washed organic solution and subject said washed organic solution to a distillation.

Nevertheless, methods for producing, purify, extract, isolate or concentrate levulinic acid that include a solvent-extraction step to yield an organic phase comprising levulinic acid, as those disclosed above, have issues related to the cost associated to high organic solvent usage. Additionally, humins and other impurities present in the organic phase can create problems in subsequent purification steps, particularly if a distillation is required, and lead to high amounts of impurities and lower concentration in the products.

Therefore, there is a clear need for new methods of producing, purifying, extracting, isolating or concentrating levulinic acid with high yield, low impurities and high concentration of the products and reduced cost.

BRIEF DESCRIPTION OF THE INVENTION

The authors of the present invention have developed a new process for the purification of levulinic acid, an aqueous solution comprising levulinic acid and a process for the production of levulinic acid.

The inventors have observed that the yield of levulinic acid and its purity is insufficient when a levulinic acid containing stream is just subjected to an organic extraction. In particular it has been surprisingly found that by performing a double extraction (an organic extraction followed by an aqueous extraction) the process of the present invention significantly improves the yield of the levulinic acid (purity over 95%) as compared to having no double extraction (purity below 85 wt %). Additionally, the products obtained by a double extraction are colorless as opposed to those obtained after a single extraction which has a yellow, reddish or brownish color indicative of the presence of humins or other residues. Thus, a double extraction significantly reduces the presence of impurities in the final products of the process of the present invention.

If further purification is performed on said aqueous solution, the additional purification steps are simplified and for example no viscous residues are generated during distillation.

In addition, since the process of the present invention is simple and inexpensive, it can be applied for large-scale purification and/or production of levulinic acid.

Therefore, a first aspect of the invention is directed to a process for the purification of levulinic acid, comprising:
  i) providing an aqueous solution comprising levulinic acid;
  ii) subjecting the aqueous solution of step (i) to an organic extraction to yield an organic solution and an aqueous solution;
  iii) subjecting the organic solution obtained in the previous step to an aqueous extraction to yield an aqueous solution, comprising levulinic acid, and an organic solution; and
  iv) subjecting the aqueous solution comprising levulinic acid obtained in step (iii) to a membrane separation to yield an aqueous solution, comprising levulinic acid, and a residue.

In a second disclosure, the present invention is directed to an aqueous solution comprising levulinic acid obtainable by a process comprising:
  i) providing an aqueous solution comprising levulinic acid;
  ii) subjecting the aqueous solution of step (i) to an organic extraction to yield an organic solution and an aqueous solution; and iii) subjecting the organic solution obtained in the previous step to an aqueous extraction to yield an aqueous solution comprising levulinic acid and an organic solution;

wherein said aqueous solution comprising levulinic acid obtained in step (iii) comprises:
between 0.01 and 27 wt % of levulinic acid; and
between 0.01 and 13.5 wt % of formic acid.

In a second aspect, the present invention is directed to a process for the production of levulinic acid from pulped lignocellulosic biomass comprising the following steps:
i. providing pulped lignocellulosic biomass;
ii. optionally subjecting the pulped lignocellulosic biomass of step (i) to a pre-hydrolysis to obtain a pre-hydrolyzed pulped lignocellulosic biomass;
iii. subjecting the pulped lignocellulosic biomass provided in step (i) or the pre-hydrolyzed pulped lignocellulosic biomass obtained in step (ii) to an hydrolysis in the presence of an acid and under conditions of temperature, time, and acid concentration to yield an aqueous slurry comprising levulinic acid;
iv. subjecting the aqueous slurry obtained in step (iii) comprising levulinic acid to a solid-liquid separation yielding to an aqueous solution comprising levulinic acid and a solid;
v. subjecting the aqueous solution obtained in step (iv) to an organic extraction to yield an organic solution and an aqueous solution;
vi. subjecting the organic solution obtained in the previous step to an aqueous extraction to yield an aqueous solution, comprising levulinic acid, and an organic solution;
vii. subjecting the aqueous solution comprising levulinic acid obtained in step (vi) to a membrane separation to yield an aqueous solution comprising levulinic acid, and a residue; and
viii. optionally, subjecting the aqueous solution comprising levulinic acid obtained in the previous step to at least one further purification to yield an aqueous solution comprising levulinic acid.

FIGURES

DETAILED DESCRIPTION OF THE INVENTION

Figure 1:
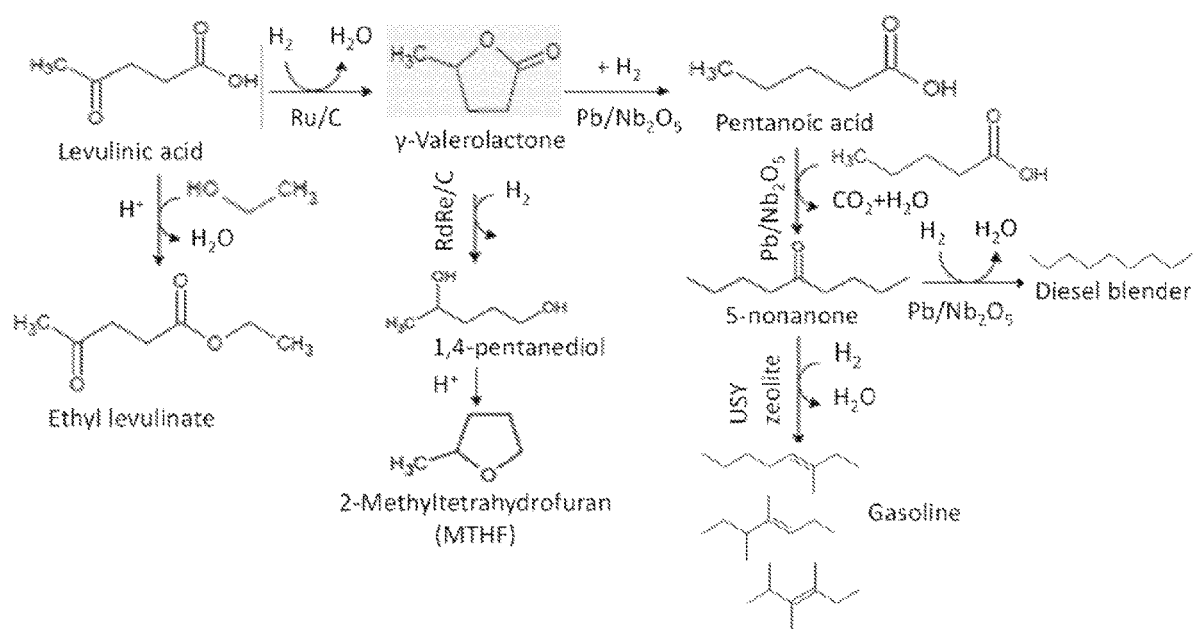
FIG. 1 shows a scheme of commercial products obtained from levulinic acid.

Unless defined otherwise, all technical and scientific terms used herein have the same meaning as commonly understood to one of ordinary skill in the art to which this disclosure belongs. As used herein, the singular forms "a" "an" and "the" include plural reference unless the context clearly dictates otherwise.

Process for the Purification of Levulinic Acid.

As defined above, in a first aspect, the present invention refers to a process for the purification of levulinic acid, comprising:
i) providing an aqueous solution comprising levulinic acid;
ii) subjecting the aqueous solution of step (i) to an organic extraction to yield an organic solution and an aqueous solution; and
iii) subjecting the organic solution obtained in the previous step to an aqueous extraction to yield an aqueous solution, comprising levulinic acid, and an organic solution; and
iv) subjecting the aqueous solution comprising levulinic acid obtained in step (iii) to a membrane separation to yield an aqueous solution, comprising levulinic acid, and a residue.

In the context of the present invention, the term "purification" refers to the separation, isolation or partial separation of a chemical substance of interest in the present invention as levulinic acid; particularly from an aqueous solution generated in the hydrolysis of biomass, particularly in the hydrolysis of lignocellulosic biomass.

In a particular embodiment the aqueous solution comprising levulinic acid of step (i) of the process of the present invention further comprises formic acid and residues; in another embodiment it further comprises formic acid and lignin residues.

In the context of the present invention, the expression "aqueous solution" refers to a solution comprising water; wherein either water or levulinic acid is the predominant compound (as opposed to an organic solution wherein usually an organic solvent is the main compound). The expression "aqueous solution" may refer to the main stream or current comprising levulinic acid such as those provided in step (i) and obtained in step (iii) and optionally in step (iv) of the process for the purification of levulinic acid or those obtained in steps (iv), (vi) and optionally (vii) of the process for the production of levulinic acid of the present invention. The aqueous solution may comprise residues, such as solid residues dispersed which can vary depending on the type of biomass used, and other compounds. A non-limitative example of an aqueous solution wherein levulinic acid is the predominant compound and water is a minor compound is the distillation solution obtained after a distillation.

In the context of the present invention the expression "residues" refers to soluble or insoluble compounds present in an aqueous solution comprising levulinic acid form which the levulinic acid need to be separated, extracted or purified from. Non-limiting examples or residues are tar, char and/or humins, lignin, carbohydrates, carboxylic acids and/or catalyst. Tar and char represent organic material dark and insoluble in water which tends to become viscous and almost black when concentrated. In the context of the present invention the term "tar" refers to an organic residue that can be formed during heating of organic material, for example by pyrolysis, and also when carbohydrates are subjected to acid hydrolysis, particularly when done at high temperatures. The term "tar" usually refers to a viscous liquid, e.g. derived from the destructive distillation of organic matter. In the context of the present invention the term "char" refers to solid material such as the remains of solid biomass that has been incompletely hydrolyzed. In the context of the present invention the term "humins" refers to organic material insoluble in water produced by acid hydrolysis of carbohydrates and lignin fraction, in the context of the present invention the term "humins" comprises the terms "tar" and "char". The presence of residues in a solution may be indicated by a dark color such a yellowish, brownish or reddish color.

Organic Extraction

The process for the purification of levulinic acid comprises a step (ii) of subjecting the aqueous solution of step (i) to an organic extraction to yield an organic solution and an aqueous solution.

In the context of the present invention, the expression "organic extraction" refers to subjecting the aqueous solution comprising levulinic acid of step (i) (liquid aqueous phase) to a solvent liquid-liquid extraction step with a water-immiscible solvent in order to yield an organic phase comprising levulinic acid that is recovered and an aqueous phase wherein part of the residues are left. In the context of the present invention the expression "organic phase" in relation with an extraction step refers to the organic solution. Similarly, the expression "aqueous phase" in relation with an extraction step refers to the aqueous solution. Generally the aqueous solution and the organic solution are immiscible between them; therefore the expression "immiscible phases" refers to the organic and aqueous phase.

In a particular embodiment, the organic extraction of step (ii) is performed using at least one water-immiscible solvent; preferably by contacting the aqueous solution provided in step (i) with a water-immiscible solvent or an organic solution; preferably a water-immiscible solvent.

In the context of the present invention, the expression "water-immiscible solvent" refers to what a skilled person would understand for.

Examples of water-immiscible solvents suitable as extracting solvents are low molecular weight ketones, ethers or acetates, such as those containing more than five carbon atoms, for example furane-derived solvents. In a preferred embodiment, the water-immiscible solvent is selected from dicholoromethane (DCM), dichloroethene (DCE), 1,2-dichloroethane, toluene, benzene, 2-heptanone, butylacetate, methylisobutylketone (MIBK), dichloromethane, ethyl 5 propionate, 2-pentanone, diethyl ether, t-amyl alcohol, butanol, cyclohexanone, ethyl acetate, pyridine, tetrahydrofuran (THF), methyltetrahydrofuran (MTHF), 2-methyl tetrahydrofuran (2-ME-THF), 2-Butanone, acetone, dioxane, acetonitrile, formamide, N,N-dimethylformamide, dimethyl sulfoxide, ethylene glycol, methyl-ter-butylether (MTBE), cyclopentyl methylether (CPMe), heptane, dimethyl formamide (DMF), N-methylpyrrolidone (NMP), 2-sec-butylphenol (SBP), 4-npentylphenol (NPP), 4-n-hexylphenol (NHP) and diethyleneglycol dimethylether (DEGDME), furfural, (hydroxymethyl)furfural, alcohol levulinate, lacone derivatives, gamma-valerolactone (GVL) and combinations thereof; preferably is selected from furfural, (hydroxymethyl)furfural, alcohol levulinate, lacone derivatives, gamma-valerolactone (GVL) methylisobutylketone (MIBK), methyltetrahydrofuran (MTHF) and combinations thereof; more preferably is selected from methylisobutylketone (MIBK), methyltetrahydrofuran (MTHF) and combinations thereof; even more preferably is methylisobutyl ketone (MIBK).

In a particular embodiment, the organic extraction of step (ii) is performed at a temperature between 20 and 100° C., preferably at room temperature.

In a preferred embodiment, the ratio water-immiscible solvent/aqueous solution of the organic extraction of step (ii) ranges from 0.25:1 to 5:1, more preferably from 1:1 to 4:1, even more preferably from 2:1 to 3.5:1.

In a particular embodiment, the organic extraction of step (ii) is performed using a water-immiscible solvent selected from dicholoromethane (DCM), dichlorcethene (DCE), 1,2-dichlorcethane, toluene, heptane, benzene, 2-heptanone, 2-Butanone, acetone, dioxane, acetonitrile, butylacetate, methylisobutylketone (MIBK), dichloromethane, ethyl 5 propionate, 2-pentanone, diethyl ether, t-amyl alcohol, butanol, cyclohexanone, ethyl acetate, pyridine, tetrahydrofuran (THF), methyltetrahydrofuran (MTHF), 2-methyl tetrahydrofuran (2-ME-THF), formamide, N,N-dimethylformamide, dimethyl sulfoxide, ethylene glycol, methyl-ter-butylether (MTBE), cyclopentyl methylether (CPMe), dimethyl formamide (DMF), N-methylpyrrolidone (NMP), 2-sec-butylphenol (SBP), 4-npentylphenol (NPP), 4-n-hexylphenol (NHP) and diethyleneglycol dimethylether (DEGDME), furfural, (hydroxymethyl)furfural, alcohol levulinate, lactone derivatives, gamma-valerolactone (GVL) and combinations thereof and combinations thereof; wherein the ratio immiscible solvent:aqueous solution is between 0.25:1 and 4:1.

In a preferred embodiment, the organic extraction of step (ii) is performed using means able for extraction, preferably extraction columns, centrifugal extractors, thin layer extractors, or a mixer-settler device; more preferably extraction columns or mixer-settler devices.

In a more preferred embodiment, the organic extraction of step (ii) is performed in a mixer-settler device; preferably by mixing the aqueous solution comprising levulinic acid of step (i) with a water-immiscible solvent or with an organic solution by stirring at between 100 and 300 rpm to obtain a mixture which is subsequently settled during between 1 and 20 min to obtain two immiscible phases; more preferably a water-immiscible solvent.

In a more preferred embodiment, the organic extraction of step (ii) is performed in an extraction column; preferably an extraction column comprising between 2 and 12 extraction stages. In an even more preferred embodiment the organic extraction of step (ii) is performed in an extraction column comprising between 2 and 12 extraction stages; wherein the aqueous solution of step (i) and the organic solution are mixed in the extraction stages during contact times of 1-20 min.

In another preferred embodiment, the organic extraction of step (ii) comprises at least one contacting step; preferably at least two contacting steps wherein in each of those steps the organic phase and the aqueous phase are in contact for at least 1 minute; preferably for at least 10 minutes; more preferably for at least 20 minutes.

In another preferred embodiment, the organic extraction of step (ii) is repeated at least once; preferably at least twice; more preferably at least three times. In a particular embodiment the process of the present invention may include multiple organic extraction steps. This may improve the efficiency of the process even more. In each step the organic phase and the aqueous phase may be in contact for at least 1 minute; preferably for at least 10 minutes; more preferably for at least 20 minutes.

In a particular embodiment, the levulinic acid or part of the levulinic acid comprised in the aqueous solution of step (i) is extracted into an organic solution (organic phase or extract) during the step (ii) of subjecting the aqueous solution to an organic extraction.

In a particular embodiment, part of the residues comprised in the aqueous solution of step (i) such as tar, lignins, carbohydrates, carboxylic acids and/or catalyst, are left in the aqueous solution obtained in the organic extraction of step (ii).

In a particular embodiment, the organic extraction of step (ii) yield an organic solution and an aqueous solution; wherein the organic solution obtained comprises levulinic acid, formic acid and the extracting water-immiscible solvent; and wherein the aqueous solution obtained comprises residues, and/or a small amount of the water-immiscible solvent; preferably the aqueous solution obtained further comprises carboxylic acids, carbohydrates, lignin compounds and/or catalyst.

In a particular embodiment, the aqueous solution obtained in the organic extraction of step (ii) is recycled; preferably is recycled by using it in other steps of the process of the present invention; preferably is recycled to the hydrolysis step. In a particular embodiment, the aqueous solution obtained in the organic extraction of step (ii) comprises a carboxylic acid and is recycled to the hydrolysis step; preferably comprises sulfuric acid.

In a more particular embodiment, the organic extraction of step (ii) yields an organic solution and an aqueous solution; wherein the organic solution obtained comprises between 0.1 and 10 wt % of levulinic acid, between 0.1 and 5 wt % of formic acid and the extracting water-immiscible solvent; more preferably between 0.3 and 7.5 wt % of levulinic acid, between 0.14 and 4 wt % of formic acid and the extracting water-immiscible solvent.

In a more particular embodiment, the organic extraction of step (ii) yields an organic solution and an aqueous solution; wherein the organic solution comprises between 0.1 and 10 wt % of levulinic acid, and between 0.05 and 5 wt % of formic acid; more preferably between 0.3 and 7.5 wt % of levulinic acid, and between 0.15 and 4 wt % of formic acid; even more preferably between 0.3 and 7.5 wt % of levulinic acid, between 0.15 and 4 wt % of formic acid and less than 0.8 wt % of residues.

In an even more particular embodiment, the organic extraction of step (ii) yields an organic solution and an aqueous solution; wherein the organic solution comprises less than 1 wt % of residues; preferably less than 0.8 wt % of residues; more preferably between 0.15 and 0.5 wt % or residues.

In an even more particular embodiment, the organic extraction of step (ii) yields an organic solution and an aqueous solution; wherein the organic solution comprises a ratio levulinic acid:residues of about 1:0.6.

The organic extraction of step (ii) has an efficiency from 85% to 97% for the levulinic and formic acid present in the aqueous solution of step (i), preferably an efficiency from 90% to 98%.

Aqueous Extraction

The process for the purification of levulinic acid comprises a step (iii) of subjecting the organic solution obtained in the previous step (in step (ii)) to an aqueous extraction to yield an aqueous solution, comprising levulinic acid, and an organic solution.

According to the present invention, the expression "aqueous extraction" refers to subjecting the organic solution comprising levulinic acid of step (ii) (organic phase) to an aqueous liquid-liquid extraction step in the presence of water or an aqueous solution (aqueous phase) in order to selectively recovering an aqueous phase comprising levulinic acid.

In a particular embodiment, the aqueous extraction of step (iii) is performed in the presence of water or an aqueous solution; preferably by contacting the organic solution comprising levulinic acid of step (ii) with water or with an aqueous solution; preferably with water or with an aqueous solution at neutral pH.

Non-limiting examples of aqueous solutions able for the aqueous extraction of step (iii) are acid, basic or neutral aqueous solutions; preferably neutral aqueous solution.

In a particular embodiment, the aqueous extraction of step (iii) is performed with and aqueous solution comprising an additive able to improve the solvation properties of the solution as known in the art; particularly a surfactant or a surfactant combination such as sulfonates, phosphates, sulfates and carboxylates.

In a particular embodiment, the aqueous extraction of step (iii) is performed with and aqueous solution having neutral pH.

In a particular embodiment, the aqueous extraction of step (iii) is performed at a temperature between 20 and 100° C., preferably at room temperature.

In a preferred embodiment, the ratio organic solution/aqueous solution of the aqueous extraction of step (iii) ranges from 0.1:1 to 1:5, more preferably from 0.25:1 to 1:3.

In a preferred embodiment, the aqueous extraction of step (iii) is performed using means able for extraction, preferably extraction columns, centrifugal extractors, thin layer extractors, or a mixer-settler device; more preferably extraction columns or mixer-settler devices.

In a more preferred embodiment, the organic extraction of step (ii) or the aqueous extraction of step (iii) are performed using means able for extraction, preferably an extraction column or a mixer-settler device; more preferably a mixer-settler device.

In a more preferred embodiment, the organic extraction of step (ii) or the aqueous extraction of step (iii) are performed at room temperature.

In a more preferred embodiment, the organic extraction of step (ii) or the aqueous extraction of step (iii) are performed by contacting and separating two immiscible phases; preferably by mixing and subsequent sedimentation of two immiscible phases.

In a more preferred embodiment, the aqueous extraction of step (iii) is performed in a mixer-settler device; preferably by mixing the organic solution comprising levulinic acid of step (ii) with a water or with an aqueous solution by stirring at between 100 and 300 rpm to obtain a mixture which is subsequently settled during between 1 and 20 min to obtain two immiscible phases.

In a more preferred embodiment, the aqueous extraction of step (iii) is performed in an extraction column; preferably an extraction column comprising between 2 and 12 extraction stages. In an even more preferred embodiment the aqueous extraction of step (iii) is performed in an extraction column comprising between 2 and 12 extraction stages; wherein the water or aqueous solution and the organic solution of step (ii) are mixed in the extraction stages during contact times of 1-20 min.

In another preferred embodiment, the aqueous extraction of step (iii) comprises at least one contacting step; preferably at least two contacting steps wherein in each step the organic phase; and more preferably at least three times. In each step the organic phase and the aqueous phase may be in contact for at least 1 minute; preferably for at least 10 minutes; more preferably for at least 20 minutes.

In another preferred embodiment, the aqueous extraction of step (iii) is repeated at least once; preferably at least twice; more preferably at least three times. In a particular embodiment the process of the present invention may include multiple aqueous extraction steps. This may improve the efficiency of the process even more.

According to the present invention, the levulinic acid or part of the levulinic acid comprised in the organic solution of step (ii) is extracted into water or into an aqueous solution during the step (iii) of subjecting the organic solution of step (ii) to an aqueous extraction. Without being bound by a particular theory, it is believed that the levulinic acid or part of the levulinic acid is extracted by solvation.

In the context of the present invention the term "solvation" describes the interaction of solvent with dissolved molecules.

In a particular embodiment, the aqueous solution obtained in step (iii) is acidic; preferably it has a pH below 7; preferably a pH between 1 and 3.

According to the present invention, part of the residues comprised in the organic solution of step (ii) such as humins are left in the organic solution obtained after the aqueous extraction of step (iii); preferably at least a 70 wt % of the residues, more preferably at least a 75 wt % of the residues; even more preferably at least about 80 wt % of the residues.

In the context of the present invention the organic solution obtained after the aqueous extraction of step (iii) can be named as "organic raffinate".

According to the present invention, by performing an aqueous extraction a significant reduction of residues (around an 80% of residues reduction) in the stream comprising levulinic acid was observed.

According to the present invention, the aqueous extraction of step (iii) yields an organic solution and an aqueous solution; wherein the aqueous solution comprises levulinic acid and formic acid; and wherein the organic solution comprises residues such as humins and water-immiscible solvent. In a particular embodiment, the aqueous solution further comprises a small amount of humins. In a particular embodiment, the organic solution obtained in step (iii) has a brownish, reddish or yellowish colour.

In a particular embodiment, the organic solution obtained in the aqueous extraction of step (iii) is recycled; preferably is recycled by using it in other steps of the process of the present invention; more preferably the organic solution is recycled by filtration, evaporation or distillation; even more preferably is evaporated yielding vapor and a concentrate, wherein said vapor is condensate and recycled.

In a more particular embodiment, the aqueous extraction of step (iii) yields an organic solution and an aqueous solution; wherein the aqueous solution comprises between 0.01 and 27 wt % of levulinic acid, and between 0.01 and 13.5 wt % of formic acid; more preferably between 0.1 and 10 wt % of levulinic acid and between 0.05 and 4 wt % of formic acid; even more preferably between 0.1 and 10 wt % of levulinic acid, between 0.05 and 4 wt % of formic acid and between 0.06 and 0.15 wt % of residues; preferably less than 0.08 wt % of residues.

In an even more particular embodiment, the aqueous extraction of step (iii) yields an organic solution and an aqueous solution; wherein the aqueous solution further comprises less than 0.1 wt % of residues; preferably between 0.06 and 0.15 wt %; more preferably less than 0.08 wt %, even more preferably about 0.06 wt % of residues.

In an even more particular embodiment, the aqueous extraction of step (iii) yields an organic solution and an aqueous solution; wherein the aqueous solution comprises a ratio levulinic acid:residues of about 1:0.1.

In a particular embodiment, the aqueous extraction of step (iii) has an efficiency of extraction between 85% and 97% for the levulinic and formic acid present in the organic solution of step (ii), preferably efficiency from 90% to 98%.

The inventors have surprisingly found that by performing a double extraction (an organic extraction followed by an aqueous extraction) the process of the present invention significantly reduces the presence of impurities and improves the yield of the levulinic acid as compared to having no double extraction. In particular, it has been observed that during the aqueous extraction most of the residues, particularly humins, are left in the organic solution obtained. In this way, an unexpected improvement of the purity of the levulinic acid, in particular of the aqueous solution comprising levulinic acid is achieved.

In a particular embodiment, the aqueous extraction of step (iii) yields an organic solution and an aqueous solution; wherein the aqueous solution has no colour; preferably is transparent.

In the context of the present invention the term "transparent" is understood as the opposite of opaque.

Further Purification

In a particular embodiment, the process as defined above in any of its embodiments, further comprises:
v) subjecting the aqueous solution comprising levulinic acid obtained in step (iii) or (iv) to at least one further purification step to yield an aqueous solution comprising levulinic acid; preferably in step (iv).

In a more particular embodiment, the at least one further purification is selected from membrane separation, filtration, evaporation, extraction, distillation, recrystallization and/or a combination thereof. Preferably the at least one further purification comprises a distillation; more preferably comprises a membrane separation followed by a distillation. In view of the composition of the aqueous solution obtained in step (iii), the skilled person can devise a further purification scheme such that an aqueous solution comprising levulinic acid is obtained.

Activated Carbon

In a particular embodiment, the at least one further purification step of step (iv) or (v) comprises subjecting the aqueous solution comprising levulinic acid obtained in step (iii), (iv) or (v) to a filtration or a membrane separation in the presence of membrane separation or filtration units comprising activated carbon; preferably filtration units comprising activated carbon.

In an alternative embodiment, the membrane separation of step (iv) or (v) is performed in the presence of powdered activated carbon. Powdered activated carbon may be directly stirred into the solution to be treated and further separation of powdered activated carbon (usually with average diameters <20 μm) may be accomplished by using filter aid and/or by membrane separation or filtration in appropriated filter systems known in the art.

In a preferred embodiment, the carbon activated purification step embodiments above are applied to step (iv) of the process for the purification of levulinic acid.

Membrane Separation

The process as defined above in any of its embodiments, further comprises a step (iv) of subjecting the aqueous solution comprising levulinic acid obtained in step (iii) to a membrane separation to yield an aqueous solution, comprising levulinic acid, and a residue.

In a particular embodiment, the membrane separation of step (iv) or (v) is selected from ultrafiltration (UF), nanofiltration (NF) and reverse osmosis (RO), preferably nanofiltration. The process of the present invention may comprise one, two or more membrane separations or units for membrane separation. Depending on the composition of the aqueous solution obtained in step (iii) or (iv) the skilled person can devise a membrane separation scheme such that an aqueous solution comprising levulinic acid is obtained.

In the context of the present invention the expression "membrane separation" involves the separation of one or more dissolved components from one or more other dissolved components. The expression "membrane separation" is to be distinguished from "filtration". In the present invention the term "filtration" is interpreted as a form of solid/liquid separation and involves particles having sizes larger than 5 micron. Membrane separation, on the other hand, relates to particles <5 micron and dissolved particles. From suspended particles of about 5 micron down to about 0.1 micron the process is termed microfiltration, while below that the term ultrafiltration applies. Ultrafiltration covers the finest distinct particles (such as 30 colloids), but its lower limits is usually set in molecular weight terms, measured in Daltons. Below ultrafiltration (UF) comes nanofiltration (NF) and reverse osmosis (RO) [Filters and Filtration Handbook, Ken Sutherland, 2008, published by Elsevier, Amsterdam]. In a particular embodiment, the membrane separation step of the present invention is performed in an aqueous solution.

In membrane separation the fraction passing through the membrane is referred to as "permeate" and the fraction retained is referred to as "retentate".

In a particular embodiment, the membrane separation of step (iv) or (v) is a nanofiltration.

According to this particular embodiment of the invention, the membrane separation of step (iv) or (v) yields an aqueous solution, comprising levulinic acid, and a residue; wherein the aqueous solution is the permeate an the residue is the retentate. In a more particular embodiment the residue or retentate of step (iv) or (v) is diluted and optionally recirculated through the membrane.

In a particular embodiment, the membrane separation of step (iv) or (v) is performed at a trans membrane pressure of between 5-60 bars, preferably between 10-50 bars, more preferably between 20-40 bars. Preferably, the membrane separation of step (iv) or (v) is performed at between 10 and 100° C., more preferably at room temperature.

In a particular embodiment, the membrane separation of step (iv) or (v) is performed at an averaged flux of between 10 and 100 l/m²·h, preferably between 20 and 80 l/m²·h; more preferably between 40 and 60 l/m²·h.

In a particular embodiment, the membrane separation of step (iv) or (v) comprises using a membrane impermeable for organic molecules. Preferably, the membrane used in the membrane separation of step (iv) or (v) is impermeable for organic molecules having a molecular weight of 300 Da or more, and can be easily selected by the skilled person based on the molecular weight cut off (MWCO). More preferably, said membrane is characterized by an approximate molecular weight cut-off of between 100-500 Dalton for uncharged organic molecules; more preferably between 150-300 Dalton.

In a particular embodiment, the membrane separation of step (iv) or (v) removes partially or totally the humins; preferably the membrane separation of step (iv) or (v) removes at least a 70 wt % of residues in the aqueous solution comprising levulinic acid obtained in step (iii) or (iv) respectively; preferably it removes all the residues left.

The MWCO, Molecular Weight Cut Off, describes the retention performance of a membrane. The expression "cut off" is defined as that molecular weight which is 90% rejected by the membrane.

In the context of the present invention, the retention percentage (R) is defined as $R=(100 \cdot (1-(C_{permeate}/C_{retentate})))$. Wherein $C_{permeate}$ is the permeate concentration and $C_{retentate}$ is the concentration retentate. A suitable handbook for membrane separation is "Basic principles of membrane technology by Marcel Mulder, published 1991 by Kluwer Academic in Dordrecht, Netherlands.

In a particular embodiment, the membrane separation of step (iv) or (v) has a retention percentage (R) for levulinic acid between 10 and 40%, preferably between 15 and 25%.

In the context of the present invention, the permeate percentage (P) is defined as $P=(100(C_{permeate}/C_{retentate}))$.

In a particular embodiment, the membrane separation of step (iv) or (v) has a permeate percentage (P) for levulinic acid is between 60 and 90%, preferably between 70 and 25%.

In the context of the invention the expression "impermeable for molecules having a molecular weight of 300 Da or more" does not necessarily mean that all molecules having a molecular weight of 300 Da or more are retained by the membrane. "Impermeable for molecules having a molecular weight of X kDa or more" means that at least 90 wt % of an X Da solute is retained by the membrane (wherein "X" refers to the molecular weight).

The membrane of the membrane separation of step (iv) or (v) is preferably a nanofiltration membrane. Nanofiltration membranes suitable for the membrane separation of the present invention are commercially available and well described in nanofiltration: Principles and Applications by Anthony Gordon Fane et al. 2005, published by Elsevier, Oxford. Well known nanofiltration membranes for acid separation in aqueous media or in aqueous solution are for example Koch MPS34 (pH 0-14), Nadir NP30 (pH 0-14), GE-Osmonics KH and DL and DK Lenntech membranes. In a particular embodiment the process of the present invention may include multiple membrane separation steps. This may improve the efficiency of the process even more.

In a particular embodiment, the membrane separation of step (iv) or (v) is preferably conducted as crossflow nanofiltration.

In a particular embodiment, the membrane separation of step (iv) or (v) may comprise diafiltration. In the diafiltration the retentate obtained by the membrane separation is washed by adding a solvent and subjected to a subsequent membrane separation. This may be repeated several times. Diafiltration may result in higher yield.

In a particular embodiment, the membrane separation of step (iv) or (v) comprises a step of adding a solvent such as water or an aqueous solution.

In a particular embodiment, the membrane separation of step (iv) or (v) is optionally repeated; preferably at least twice; more preferably at least three times.

In a particular embodiment, the aqueous solution obtained in step (iv) or (v) is clear; preferably transparent.

In a particular embodiment, the aqueous solution comprising levulinic acid obtained in step (iii) comprises at least a 0.1 wt % of levulinic acid.

In a particular embodiment, the aqueous solution comprising levulinic acid obtained in steps (iii) or (iv) or (v) comprises at least a 0.1 wt % of levulinic acid, preferably at least 0.5 wt %.

In a more particular embodiment, the aqueous solution obtained in step (iv) or (v) further comprises formic acid; preferably at least a 0.01 wt % of formic acid.

In a preferred embodiment, the carbon membrane separation embodiments above are applied to step (iv) of the process for the purification of levulinic acid.

The inventors have found that by working through most of the process in an aqueous solution, more resistant and cheaper materials can be used for the membranes of the membrane separation of the present invention than by working in an organic solution.

In addition, it has been observed that by performing the membrane separation in an aqueous media, the aqueous solution obtained after said membrane separation comprises carboxylic acids such as formic acids, in addition to levulinic acid, which increases the value of the final products.

It has been also observed that the nanofiltration of the aqueous solution comprising levulinic acid obtained in step (iii) leads to an aqueous solution (permeate) without residues such as humins or lignin residues with low molecular weight. This further increases the efficiency of the process of the present invention.

Distillation

In a particular embodiment, the process as defined above in any of its embodiments further comprises: subjecting the aqueous solution comprising levulinic acid obtained in step (iv) or in step (v) to a distillation to yield a distillate and a distillation solution comprising levulinic acid. In an embodiment, the main compound in the distillation solution is levulinic acid. In an embodiment, the distillation step of the process of the present invention is selected from single distillation, multi-stage steam distillation, vacuum distillation, flash distillation or a combination thereof; more preferably is a vacuum distillation.

In a more particular embodiment, the vacuum distillation of the present invention is performed at reduced pressure, preferably at between 20 and 500 mbar, more preferably at between 40 and 400 mbar, even more preferably at between 50 and 300 mbar.

In a more particular embodiment, the vacuum distillation of the present invention is performed at a bottom temperature of between 10 and 100° C., preferably between 20 and 80° C., more preferably between 30 and 70° C.

In the context of the present invention the term "distillate" is related to the overhead stream of a distillation unit as understand by an expert in the art. In a particular embodiment the distillate of the distillation present invention comprises formic acid; preferably between 0.01 and 0.5 wt % of formic acid; more preferably between 0.1 and 0.4 wt % of formic acid; even more preferably around 0.2 wt % of formic acid.

In a more particular embodiment the distillate of the distillation present invention comprises water, formic acid and solvent, preferably comprises a 98.3 wt. % of water, a 0.2 wt % of formic acid and a 1.5 wt % of water-immiscible solvent.

In the context of the present invention the term "distillation solution" is related to the bottom stream of a distillation unit as understand by an expert in the art. In a particular embodiment the distillation solution of the present invention comprises levulinic acid. In a particular embodiment the distillation solution of the present invention comprises at least 90 wt % of levulinic acid; preferably at least 95 wt % of levulinic acid. In a more particular embodiment the distillation solution of the present invention comprises between 85 and 99 wt % of levulinic acid; more preferably comprises between 90 and 98 wt % of levulinic acid. More preferably the distillation solution of the present invention comprises levulinic acid, lactone and lactone oligomers; even more preferably the distillation solution of the present invention comprises between 90 and 97 wt % of levulinic acid and lactone and lactone oligomers.

In the context of the present invention the term "distillation" may comprise a single distillation step or a multiple distillation steps and/or units. A purified levulinic acid may be recovered as a distillate and/or as a distillation solution; preferably as distillation solution in the bottom stream. The distillation step may comprise multiple distillation units (such a train distillation). If the process comprises multiple distillation units, levulinic acid may be recovered as a distillate or residue from an intermediate distillation unit. Thus, depending on the composition of the aqueous solution obtained in steps (iv) or (v) the skilled person can devise a distillation scheme such that the levulinic acid is suitably recovered.

The presence of residues such as humins and tar in distillation processes presents a problem, because those components are difficult to process in terms of flowing and pumping. The inventors have observed that, when subjecting the aqueous solution comprising levulinic acid obtained in step (iv) or (v) to a distillation to yield a distillate and a distillation solution comprising levulinic acid, surprisingly no dark and viscous residues are left in the distillation solution thus, facilitating removal of the distillation residue from the distillation unit. Moreover, by performing a double extraction followed by a membrane separation, mild conditions such as low distillation temperatures are enough to obtain a concentrated levulinic acid with high purity and with a few or none lactone compounds related with levulinic acid degradation left in the distillation solution.

Evaporation

In a particular embodiment, the process of the present invention as defined above in any of its embodiments further comprises: subjecting to a partial evaporation step any of the following solutions: the aqueous solution provided in step (i), or obtained in step (iii) or in step (iv) or in step (v), the organic solution obtained in step (ii), or any combination of them. In an even more particular embodiment, any of the aqueous or organic solutions obtained in any of the steps of the process of the present invention are subjected to a partial evaporation step. In an even more particular embodiment, any of the aqueous or organic solutions obtained in any of the steps of the process of the present invention can be subjected to a recirculation step. In another more particular embodiment, any of the aqueous or organic solutions obtained in any of the steps (number of step n) of the process of the present invention can be subjected to a recirculation step to the step immediately before (n−1) or to previous ones (n−2).

In a particular embodiment, the evaporation step of the process of the present invention is performed in a unit selected from thin-film evaporator, wiped film evaporator, falling film evaporator, forcer circulator evaporator, scrapped surface evaporator and agitated thin film evaporator, preferably a thin-film evaporator. In more a particular embodiment, the evaporation step of the process of the present invention is performed at between 20 and 160° C. and at a pressure of between 150-200 mbars.

In a more particular embodiment the organic solution obtained in step (ii) is subjected to an evaporation to yield an organic solvent vapor (or water-immiscible solvent) and a concentrated organic solution. In a particular embodiment, the concentrated organic solution is further subjected to the aqueous extraction of step (iii). In an even more particular embodiment said solvent vapor can be condensed and reused in the organic extraction step (ii) of the present invention.

The optional evaporation of the organic solution obtained in step (ii) leads to a reduction of the total amount of organic solvent used in the whole process since the vapors produced during the evaporation may be recycled.

In a more particular embodiment the aqueous solution provided in step (i) or obtained in step (iii) or (iv) or (v) is subjected to an evaporation to yield a water vapor and a concentrated aqueous solution. In a particular embodiment, the concentrated aqueous solution is further subjected to the organic extraction of step (ii). In a particular embodiment, the concentrated aqueous solution is further subjected to the membrane separation of step (iv). In a particular embodiment, the concentrated aqueous solution is further subjected to a distillation. In an even more particular embodiment, said water vapor can be condensed, recirculated and reused in the aqueous extraction step (iii) of the present invention.

When any of the aqueous solution is subjected to an evaporation step the amount of total water used in the whole process is reduced by recycling the water vapor, this water saving is especially relevant when the evaporation is performed to the aqueous solution obtained in step (iii) or to the permeate obtained after a membrane separation step. Additionally, by using an evaporation step, the global efficiency of the process is increased.

Aqueous Solution of Step (i)

In a particular embodiment, the process of the present invention as defined above in any of its embodiments further comprises that the aqueous solution comprising levulinic acid of step (i) is obtained by i. providing a pulped lignocellulosic biomass;
ii. optionally subjecting the pulped lignocellulosic biomass of step (i) to a pre-hydrolysis to obtain a pre-hydrolyzed pulped lignocellulosic biomass;
iii. subjecting the pulped lignocellulosic biomass provided in step (i) or the pre-hydrolyzed pulped lignocellulosic biomass obtained in step (ii) to an hydrolysis in the presence of an acid and under conditions of temperature, time, and acid concentration to yield an aqueous slurry comprising levulinic acid; and
iv. subjecting the aqueous slurry comprising levulinic acid obtained in step (iii) to a solid-liquid separation yielding to an aqueous solution comprising levulinic acid and a solid.

In a more particular embodiment, the process as defined above in any of its embodiments further comprises that the pulped lignocellulosic biomass is obtained by:

a) providing biomass comprising a lignocellulosic material;
b) optionally, subjecting said biomass to a mechanical treatment; and
c) dispersing said biomass in a solvent to obtain pulped lignocellulosic biomass.

Biomass

In the context of the present invention, the term "biomass" and in particular the expression "biomass comprising a lignocellulosic material" refers to biological material from living, or recently living, plants or plant-derived materials. Any lignocellulosic material, such as hard or soft wood, grasses, agricultural waste, food waste, other plant material, municipal waste, or a combination of one or more biomass materials can be used as biomass in the process of the present invention. Examples of wood useful in the process of the invention include pine, *Eucalyptus*, olive, poplar, fir, sprice, larch, beech, oak, and palm trees and palm waste. The material may include wood form trunks, stems, branches, roots, heartwood, wood trimmings, wood bark, saw dust, wood pruning and forest residue. Agricultural material or waste which may be used in the process of the invention include, corn stover, corn cobs, corn kernels, corn fibers, straw, banana plantation waste, rice straw, rice hull, oat straw, oat hull, cotton stalk, cotton gin, wheat straw, sugar cane bagasse, sugar cane trash, sorghum residues, sugar processing residues, bread processing residues, barley straw, cereal straw, canola strew and soybean stover, for example. Examples of food waste include, among others, bread waste, rice, fruit or vegetables waste, such as orange pulp or orange peel. Grasses may include switchgrass, cordgrass, ryegrass, miscanthus, Bermuda grass, reed canary grass, and alfalfa. Other plant material may include wood and non-wooden plant material including stems, stalks, shrubs, foliage, bark, roots, pods, nuts, husks, fibers, vines and algae. Municipal waste may include residential waste such as waste paper and food industrial waste such as paper waste and board, paper-mill sludge and other cellulosic waste.

In a preferred embodiment, the biomass of step a) is cellulosic biomass; more preferably lignocellulosic biomass.

In a more preferred embodiment, the biomass of step a) has at least 5% by weight of cellulosic material, more preferably at least 10% by weight of cellulosic material, even more preferably at least 25% by weight of cellulosic material.

Mechanical Treatment

In a particular embodiment, the biomass comprising a lignocellulosic material of step (a) is subjected to a mechanical treatment.

The biomass comprising lignocellulosic material of step (a) may be introduced into a preparation system from storage or directly from transit. It may be passed through bag slitting or other automated decontainerization process if required, and then to a metal detection and removal process and/or pressure or other washing process in which dirt and stones are removed from the biomass.

The biomass of step (a) may then be conveyed and processed in a drying system, such as an air blaster or other drying system, to remove excess surface water. The clean biomass may then be passed on to one or more comminution stages.

In a more particular embodiment, the biomass is subjected to a mechanical treatment to obtain said biomass in particulate form.

In preferred embodiment, the mechanical treatment of step b) is comminution. The biomass of step b) may undergo comminution, such as by creating chips or flakes in order to attain a desired particle size. This may be done, for example, by a flaking and sieving machine or a knife ring flaker with vibratory screen.

Particle size is chosen so as to keep the biomass in suspension and to permit heat transfer through the biomass within the reactor system where the hydrolysis takes place subsequently, since the heat transfer depends on biomass density and biomass shape, among other similar factors. In some embodiments, the biomass is in a particulate form of about 0.5 to 5 mm thick and about 12 to 80 mm in width and length, more preferably to about 0.5 to 1.5 mm thick and about 12 to 15 mm in width and length. Preferred biomass particulate sizes can also be expressed in terms of equivalent diameters of spherical particles. Accordingly, preferred sizes may be about 5 to 10 mm in equivalent diameter. In some embodiments having cylindrical sections, such as grass type feedstocks, preferred sizes may be about 2 to 5 mm in diameter and 25 to 50 mm in length. Particle size is a function of the system capacity and hence dimensions, as well as feedstock, so that some embodiments may employ other size ranges.

In some embodiments, the biomass comprising lignocellulosic material (starting material) may be comprised of many different materials, such as bark, twigs and leaves. Processing such material to reduce its size also makes the material more homogeneous and therefore better suited to processing. At the desired thickness, such as that described above, heat transfer to the center of the biomass is sufficiently quickly, making it a useful size for use in the hydrolysis reactor described further below.

In a preferred embodiment of the invention, the biomass comprising lignocellulosic material is subjected to a mechanical treatment to obtain the biomass in particulate form having a desired particle size according to step (b) of the process of the invention.

In a more particular embodiment, the mechanical treatment of step (b) is grinding. For example, the biomass may be chopped up into small pieces using an attritor or grinder to reduce the solid to a fine powder. More preferably, the biomass or lignocellulosic material is subjected to a milling process to obtain a particulate material in powder form having particle sizes ranging from 200 to 500 µm. In a more preferred embodiment, the particle size ranges from 200 to 300 µm. This milling process may be carried out using a concentric ring grinder.

In a more particular embodiment, the mechanical treatment of step b) comprises a step of air removing. In some embodiments, the biomass may be further processed to remove air from it. This may be achieved by applying vacuum to the biomass and/or displacing air in the biomass with an inert gas such as CO2 or nitrogen. In some embodiments, the biomass material is placed under vacuum or partial vacuum and an inert gas is drawn into the material, displacing the air and removing oxygen from the material. The removal of oxygen from the material is desirable in order to reduce the level of oxidative degradation of products and other undesirable reaction mechanisms, which may increasingly occur at elevated temperatures and pressures and in the presence of acidic catalysts, as in the case of the process of the invention. The yield of sugars and other preferred products may be reduced by oxidative degradation, thus leading to reduced yields of fuel and other secondary products.

The provision of the biomass or lignocellulosic material may optionally include the removal and collection of volatile and other non-lignocellulosic components such as essential oils, terpenes, amino acids, etc. The volatile components, such as residual gases, low molecular weight organics and some oils and lipids, can be removed from the biomass by single or multi-stage steam distillation or flash volatilization. Other non-lignocellulosic components may be removed by processes already known by a skilled person, such as through one or more extraction steps using one or more solvents.

In some embodiments, the solid biomass is dewatered to remove loose surface water, as may be required for further processing. For example, the water may be removed by using a high pressure press or a superheated steam reactor. In some embodiment, the solid biomass has a water content of more than about 60% before dewatering. After dewatering, the water content of the biomass may be reduced to less than about 60%, such as about 50%.

The pulped lignocellulosic biomass of the present invention is obtained by a process comprising a step (c) of dispersing biomass in a solvent to obtain pulped lignocellulosic biomass.

In a preferred embodiment, the solvent of step (c) is water or an aqueous solution. In another preferred embodiment the biomass and the solvent of step (c), are pre-mixed in a separate tank which may be equipped with a stirrer. As a result, an aqueous slurry containing pulped lignocellulosic biomass is obtained.

In a particular embodiment, the pulped lignocellulosic biomass provided according to the processes described herein above, comprises solid biomass and water or an aqueous solution; preferably the ratio solid biomass:water/aqeuous solution is 10:1. In a preferred embodiment, said solid biomass comprises cellulose, hemicellulose and lignin. In some embodiments, on a dry basis, the solid biomass is about 40-50 wt % cellulose, about 25-35 wt % hemicellulose and about 15-20 wt % lignin, with small amounts of insoluble, such as inorganic salts.

Pre-Hydrolysis

In a particular embodiment, the process of the present invention as defined above in any of its embodiments further comprises that the aqueous solution comprising levulinic acid of step (i) is obtained by a process comprising
i. providing a pulped lignocellulosic biomass; and
ii. optionally subjecting the pulped lignocellulosic biomass of step (i) to a pre-hydrolysis.

In a particular embodiment, said pulped lignocellulosic biomass is subjected to a pre-hydrolysis, preferably in a reactor.

In a more particular embodiment, said pre-hydrolysis is in the presence of an acid or as auto-hydrolysis; preferably said pre-hydrolysis is in the presence of an acid under conditions of temperature, time, and acid concentration.

In more particular embodiment, said acid pre-hydrolysis is performed in presence of sulfuric acid at a temperature between 100 and 150° C., a pressure of between 1 and 5 barg and during a period of time between 0.5 and 4 hours.

In a particular embodiment, said pre-hydrolysis is performed as an auto-hydrolysis in the absence of an external acid catalyst.

In more particular embodiment, said auto-hydrolysis is performed at a temperature between 150 and 200° C., a pressure of between 2 and 6 barg and during a period of time between 4 and 8 hours.

In a more particular embodiment said pre-hydrolysis removes or partially removes the hemicellulose fraction from the pulped lignocellulosic biomass.

In an even particular embodiment, the process of the present invention as defined above in any of its embodiments further comprises that the aqueous solution comprising levulinic acid of step (ii) is subjected to a solid-liquid separation yielding an aqueous solution comprising levulinic acid, and a solid.

The authors of the present invention have observed that when the pulped lignocellulosic biomass is subjected to a pre-hydrolysis step, the yield of levulinic acid, its purity and the efficiency of the overall process is enhanced. Also, the additional purification steps such as the extraction steps are improved and simplified since, for example, less furan residues are generated during the pre-hydrolysis and hydrolysis steps.

Hydrolysis

In a particular embodiment, the process of the present invention as defined above in any of its embodiments further comprises that the aqueous solution comprising levulinic acid of step (i) is obtained by a process comprising a step (iii) of subjecting the pulped lignocellulosic biomass provided in step (i) or (ii) to an acid hydrolysis in the presence of an acid and under conditions of temperature, time, and acid concentration to yield an aqueous slurry comprising levulinic acid.

In another preferred embodiment, the hydrolysis of step (iii) is performed in the presence of an acid catalyst; preferably said acid is preferably selected from formic acid, poliacids, hydrochloric acid, sulphuric acid, phosphoric acid, paratoluensulfonic acid and hydrobromic acid; more preferably is selected from hydrochloric acid, sulphuric acid, phosphoric acid, paratoluensulfonic acid and hydrobromic acid; even more preferably is sulphuric acid.

In a more preferred embodiment, the acid of the pre-hydrolysis of step (ii) or the hydrolysis of step (iii) is in a weight percentage ranging between 1 and 10% with respect to the total weight of the mixture, more preferably between 1 and 5%, even more preferably at between 2 and 4%.

In a preferred embodiment, the pulped lignocellulosic biomass of the pre-hydrolysis of step (ii) or the hydrolysis of step (iii) is present in a weight percentage ranging between 5 and 50% with respect to the total weight of the mixture, more preferably between 5 and 25%, even more preferably between 5 and 15%.

In another preferred embodiment, the pre-hydrolysis of step (ii) or the hydrolysis of step (iii) is performed in the presence of a further catalyst; preferably a further catalyst selected from acids, zeolites, solid acids and chloride salts; more preferably chloride salts. More preferably, the catalyst is in a weight percentage ranging between 1 and 15% with respect to the total weight of the mixture, more preferably between 2 and 11%, even more preferably at about 2%.

In a more particular embodiment, the remaining percentage of the mixture of the pre-hydrolysis of step (ii) or the hydrolysis of step (iii) is water.

In a particular embodiment, the hydrolysis of step (iii) is performed at a temperature between 150° and 200° C., more preferably at between 165 and 190° C., even more preferably at about 180° C. Preferably, is performed in a hermetic hydrolysis reactor, more preferably in a tank-type reactor which may also be equipped with a stirrer to further improve the mixing of the components. If the temperature is too high, substantial, unwanted, decomposition of the components of the mixture may occur and the reactor pressure may be too high. If the temperature is too low, the conversion of hydroxymethylfurfural to levulinic acid may be too slow.

In a particular embodiment, the hydrolysis of step (iii) is performed at a pressure between 5 and 15 bargs, preferably between 7 and 10 bargs. More particularly, said pressure is reached autogenously. In the context of the present invention the term "barg" refers to gauge pressures as understand by an expert in the art for example, 7 barg means a gauge pressure of 7 bar.

In a particular embodiment, the hydrolysis of step (iii) is performed during between 0.5 and 4 h, preferably between 1 and 3 hours, more preferably between 1 and 3 hours. If the average residence time is too short, the degradation of the desired products may not be complete and on the contrary, if the average residence time is too long, the efficiency of the system may diminish by apparition of humins substances.

During the hydrolysis, the cellulose contained in the biomass is degraded by the acid in a first step to hexose monomers and oligomers, whereas hemicellulose degrades to both hexose and pentose monomers and oligomers. The pentose monomers and oligomers are further degraded to furfural and the hexose monomers are further degraded to hydroxymethylfurfural. In a second step, part of the furfural is converted to formic acid, whereas the hydroxymethylfurfural is converted to levulinic acid. During the hydrolysis and/or pre-hydrolysis residues may be generated.

In a particular embodiment, the aqueous slurry comprising levulinic acid obtained in step (iii) is left to cool down to room temperature.

In a particular embodiment, aqueous slurry comprising levulinic acid obtained in step (iii) comprises a 2.6 wt % of levulinic acid.

In a particular embodiment, the aqueous slurry comprising levulinic acid obtained in step (iii) further comprises residues.

Solid-liquid Separation

In a particular embodiment, the process of the present invention as defined above in any of its embodiments further comprises that the aqueous solution comprising levulinic acid of step (i) is obtained by a process comprising a step (iv) of subjecting the aqueous slurry comprising levulinic acid obtained in step (iii) to a solid-liquid separation yielding to an aqueous solution comprising levulinic acid, and a solid.

In a particular embodiment, the solid of step (iv) is subjected to a washing step with water or with an aqueous solution yielding an aqueous solution comprising levulinic acid. In an embodiment, said aqueous solution comprising levulinic acid can be optionally added to the aqueous solution obtained in the solid-liquid separation. In an embodiment the washing step comprises multiple washing steps.

In a particular embodiment the solid-liquid separation of step (iv) is performed by filtration, sedimentation, centrifugation and/or a combination thereof; preferably by filtration.

In a particular embodiment, the aqueous solution obtained in step (iii) or in step (iv) comprises between 0.5 and 3 wt % of levulinic acid, preferably between 1 and 2.5 wt % of levulinic acid, more preferably between 1.5 and 2.5 wt % of levulinic acid.

In a particular embodiment, the aqueous solution obtained in step (iii) or in step (iv) further comprises between 0.5 and 3 wt % of formic acid, more preferably between 0.75 and 1 wt % of formic acid.

In a particular embodiment, the aqueous solution obtained in step (iii) or in step (iv) further comprises residues.

In a particular embodiment, the aqueous solution obtained in step (iii) comprises between 1.5 and 2.5 wt % of levulinic acid and between 0.75 and 1 wt % of formic acid.

Aqueous Solution

In a second disclosure, the present invention is directed to an aqueous solution comprising levulinic acid obtainable by a process comprising:
 i) providing an aqueous solution comprising levulinic acid;
 ii) subjecting the aqueous solution to an organic extraction to yield an organic solution and an aqueous solution; and
 iii) subjecting the organic solution obtained in the previous step to an aqueous extraction to yield an aqueous solution comprising levulinic acid and an organic solution;
wherein said aqueous solution comprising levulinic acid obtained in step (iii) comprises:
 between 0.01 and 27 wt % of levulinic acid; and
 between 0.01 and 13.5 wt % of formic acid.

In a particular embodiment, the aqueous solution comprising levulinic acid obtained in step (iii) comprises:
 between 0.1 and 10 wt % of levulinic acid;
 between 0.05 and 4 wt % of formic acid; and
 between 0.06 and 0.15 wt % of residues.

Production of Levulinic Acid

In a second aspect, the present invention is directed to a process for the production of levulinic acid from a pulped lignocellulosic biomass comprising the following steps:
 i) providing pulped lignocellulosic biomass;
 ii) optionally subjecting the pulped lignocellulosic biomass of step (i) to a pre-hydrolysis to obtain a pre-hydrolyzed pulped lignocellulosic biomass;
 iii) subjecting the pulped lignocellulosic biomass provided in step (i) or the pre-hydrolyzed pulped lignocellulosic biomass obtained in step (ii) to an hydrolysis in the presence of an acid and under conditions of temperature, time, and acid concentration to yield an aqueous slurry comprising levulinic acid;
 iv) subjecting the aqueous slurry obtained in step (iii) comprising levulinic acid to a solid-liquid separation yielding to an aqueous solution comprising levulinic acid and a solid;

v) subjecting the aqueous solution obtained in step (iv) to an organic extraction to yield an organic solution and an aqueous solution;

vi) subjecting the organic solution obtained in the previous step to an aqueous extraction to yield an aqueous solution, comprising levulinic acid, and an organic solution;

vii) subjecting the aqueous solution comprising levulinic acid obtained in step (vi) to a membrane separation to yield an aqueous solution comprising levulinic acid, and a residue; and viii) optionally subjecting the aqueous solution comprising levulinic acid obtained in the previous step to at least one further purification to yield an aqueous solution comprising levulinic acid.

In a particular embodiment, the further purification of step (viii) is a distillation; preferably a vacuum distillation.

In a particular embodiment, the further purification of step (viii) is an evaporation.

In a preferred embodiment, the further purification of step (viii) is a membrane separation followed by a distillation; preferably a membrane separation followed by a vacuum distillation.

In a particular embodiment, the aqueous solution comprising levulinic acid obtained in step (vi) comprises at least a 0.1 wt % of levulinic acid.

In a preferred embodiment, the aqueous solution comprising levulinic acid obtained in step (vi) or in step (vii) or in step (viii) comprises at least a 0.1 wt % of levulinic acid.

In a more preferred embodiment, the aqueous solution comprising levulinic acid obtained in step (vi) or in step (vii) or in step (viii) comprises between 0.01 and 27 wt % of levulinic acid; more preferably between 0.01 and 27 wt % of levulinic acid and between 0.01 and 13.5 wt % of formic acid; even more preferably between 0.1 and 10 wt % of levulinic acid, between 0.05 and 4 wt % of formic acid, and between 0.06 and 0.15 wt % of residues.

In a preferred embodiment, the aqueous solution comprising levulinic acid obtained in step (vii) or in step (viii) comprises between 85 and 99 wt % of levulinic acid; more preferably comprises between 90 and 98 wt % of levulinic acid. In an embodiment, the aqueous solution comprising levulinic acid obtained in step (vii) or in step (viii) may have levulinic acid as a main compound, formic acid and residues.

In a more particular embodiment the further purification of step (viii) is a distillation to yield a distillate and a distillation solution comprising levulinic acid; wherein the distillation solution comprises at least 90 wt % of levulinic acid.

In a more particular embodiment, the aqueous solution obtained in steps (iv), (vi), (vii) or (viii), the organic solution obtained in step (v), or any combination of them, are subjected to a partial evaporation step. In an even more particular embodiment, any of the aqueous or organic solutions obtained in any of the steps of the process of the present invention are subjected to a partial evaporation step. In an even more particular embodiment, any of the aqueous or organic solutions obtained in any of the steps of the process of the present invention can be subjected to a recirculation step.

In a particular embodiment, the aqueous solution comprising levulinic acid obtained in steps (vii) or (viii) is subjected to a distillation to yield a distillate and a distillation solution comprising levulinic acid; preferably wherein the distillation solution comprises at least 90 wt % of levulinic acid.

In an even more particular embodiment the further purification of step (viii) is a membrane separation followed by a distillation to yield a distillate and a distillation solution comprising levulinic acid; wherein the distillation solution comprises at least 95 wt % of levulinic acid.

In a particular embodiment, the pulped lignocellulosic biomass of the process for the production of levulinic acid as described above in any of its embodiments is obtained by:

a) providing biomass comprising a lignocellulosic material;

b) optionally, subjecting said biomass to a mechanical treatment; and c) dispersing said biomass in a solvent to obtain pulped lignocellulosic biomass.

All the particular embodiments described above for the process for the purification of levulinic acid regarding the pre-hydrolysis, hydrolysis, solid-liquid separation, organic extraction, aqueous extraction, membrane separation and/or further purification steps, also apply to the process for the production of levulinic acid with the corresponding renumbering of the step numbers.

Levulinic Acid Application

The levulinic acid thus prepared may be used to produce liquid fuels as well as fuel additives. In particular, levulinic acid may be subjected to a hydrogenation process in the presence of a metal catalyst to obtain valerolactone which is a precursor of liquid fuels such as gasoline, 2-methyltetrahydrofuran and diesel blenders. In addition, levulinic acid may also be subjected to esterification in order to obtain levulinate esters, such as ethyl levulinate or butyl levulinate, which are precursors of fuel additives.

FIG. 1 shows a scheme of commercially-interesting products obtained from levulinic acid.

The aqueous solution comprising levulinic acid and the process for the production of levulinic acid from a pulped lignocellulosic biomass present all the advantages and characteristics as defined above for the process for the purification of levulinic acid of the present invention in any of its embodiments.

In particular, the process steps of the process for the production of levulinic acid from a pulped lignocellulosic biomass present all the advantages and characteristics as defined above for the process for the purification of levulinic acid of the present invention in any of its embodiments.

Embodiment of the Invention

Figure 2:
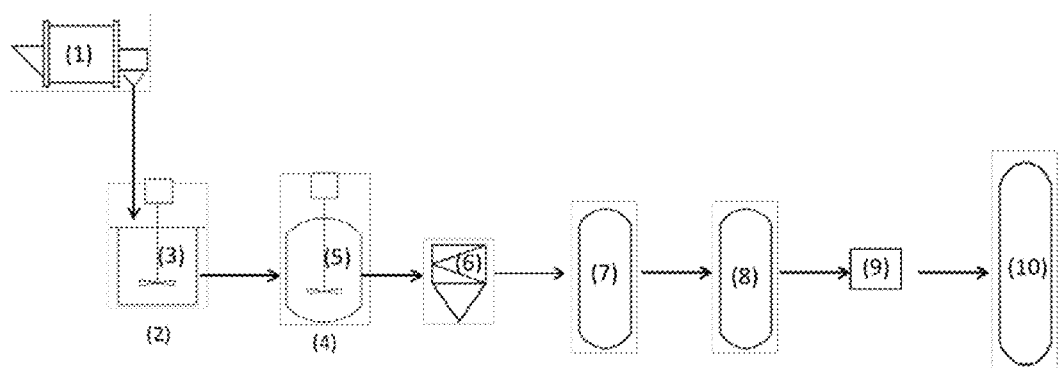
FIG. 2 shows a diagram illustrating a preferred embodiment of this invention. Reference is made hereto in the following description.

The accompanying FIG. 2 is a diagram illustrating a preferred embodiment of this invention. Reference is made hereto in the following description.

Step 1. Mechanical Pre-Treatment and Slurry Formation

Biomass or a lignocellulosic material containing at least 25% by weight of cellulose is subjected to a mechanical pre-treatment by introducing the biomass in an attritor or grinder (1). This mechanical pre-treatment reduces the starting material to a fine powder. Preferably, this pre-treatment consists in a milling process which allows obtaining a particulate material in powder form in a short period of time, having particle sizes ranging from 200 to 500 μm. In a more preferred embodiment, the particle size ranges from 200 to 300 μm.

The pre-treated biomass is fed to a mixing tank (2) which is provided with a stirrer (3). An aqueous solution is also discharged to the mixing tank (2) resulting in an aqueous slurry containing the pre-treated biomass.

Step 2. Acid Hydrolysis

An acid is discharged to the mixing tank (2) comprising the biomass slurry. Said acid is preferably selected from formic acid, poliacids, hydrochloric acid, sulphuric acid, phosphoric acid, paratoluensulfonic acid and hydrobromic acid; more preferably is sulphuric acid.

In a preferred embodiment, the pre-treated biomass is added to in a weight percentage ranging between 5 and 50% with respect to the total weight of the slurry, more preferably between 5 and 25%, even more preferably between 5 and 15%.

In another preferred embodiment, a catalyst is added in a weight percentage ranging between 1 and 15% with respect to the total weight of the slurry, more preferably between 2 and 11%, even more preferably at about 2%.

In another preferred embodiment, an acid is added in a weight percentage ranging between 1 and 10% with respect to the total weight of the slurry, more preferably between 2 and 4%, even more preferably at about 4%.

The remaining percentage corresponds to water.

All the components of the slurry are stirred in the mixing tank (2) at room temperature. As a result, aqueous slurry containing the pre-treated biomass, the acid and a catalyst is obtained which is fed to the hydrolysis reactor (4) which is also equipped with a stirrer (5) to further improve the mixing of the components.

For the acid hydrolysis to start, heat is supplied to the hydrolysis reactor (4). The reaction is exothermic and, once started, it produces sufficient heat for the duration of the reaction. The hydrolysis reaction is carried out at a temperature ranging from 170° and 200° C., more preferably at between 165-180° C. under autogenous pressure of between 10 to 12 barg; preferably between 7 to 10 barg.

The residence time the mixture spends in the reactor during the acid hydrolysis ranges from 0.5 to 4 hours, preferably about 60-180 minutes.

After the reaction is complete, the temperature of the reacted mass is reduced to room temperature in a controlled manner. This cooling step is performed gradually during at least 50 minutes. The reacted mixture mainly includes levulinic acid, formic acid, acid, solid residues and water, as well as minor amount of furfural.

This aqueous slurry comprising levulinic acid (reacted mass) is then discharged from the hydrolysis reactor to a low pressure zone to flash off some of the undesirable components of the aqueous slurry comprising levulinic acid, such as non-condensable vapours.

Step 3. Filtration and Washing

The aqueous slurry comprising levulinic acid is then fed to a filtration zone (6) to separate the solid residue and to discharge the resulting hydrolysate liquor, i.e. the liquid mixture resulting from the separation of the solid residue (aqueous solution comprising levulinic acid), to the solvent extraction vessel (7).

The solid residue is washed with water at room temperature, and the resulting washed liquor, which contains a portion of the levulinic acid and formic acid, is recycled and also fed to the extraction vessel (7) to be added to the liquid mixture resulting from the separation of the solid residue.

Step 4. Solvent Extraction

The liquid aqueous mixture fed to the extraction vessel (7) (aqueous solution comprising levulinic acid) is subjected to a solvent extraction step in the presence of a water-immiscible solvent in order to selectively recover an organic phase comprising levulinic acid (and formic acid) and to obtain an aqueous solution. Said aqueous solution may be used to recycle the acid catalyst.

The Examples of water-immiscible solvents suitable as extracting solvent are low molecular weight ketones, ethers or acetates, such as those containing more than five carbon atoms, for example furane-derived solvents. In a preferred embodiment, the water-immiscible solvent is selected from methyl isobutyl ketone (MIBK) and 2-methyltetrahydrofuran (MTHF).

In a preferred embodiment, the ratio water-immiscible solvent/aqueous solution is between 0.25:1 and 1:5, preferably is 2:1.

In another preferred embodiment, the solvent extraction comprises at least two contacting steps, wherein the organic phase and the aqueous phase are in contact for at least 60 minutes.

The compounds in the extraction vessel are extracted into (i) an organic phase (extract) containing levulinic acid, formic acid, a minor amount of furfural and the extracting water-immiscible solvent; and (ii) an aqueous phase (raffinate) containing acid catalyst and a small amount of the water-immiscible solvent.

Step 5. Aqueous Extraction

The organic phase (extract) fed to the extraction vessel (8) is subjected to an aqueous extraction step in the presence of water or of an aqueous solution solvent in order to selectively recover an aqueous phase comprising levulinic acid (and formic acid).

In a preferred embodiment, the ratio water-immiscible solvent/aqueous solution is between 0.25:1 and 1:3, preferably is 1:1.

In another preferred embodiment, the aqueous extraction comprises at least two contacting steps, wherein the organic phase and the aqueous phase are in contact for at least 5 minutes.

The compounds in the extraction vessel are extracted into (i) an aqueous phase comprising levulinic acid, formic acid and the extracting water-immiscible solvent; and an organic phase (organic raffinate) comprising residues, in particular humins.

Additionally, the aqueous phase comprising levulinic acid above can optionally suffer a nanofiltration step (9) and a distillation step (10) in order to obtain an aqueous phase comprising purified levulinic acid.

The present invention will now be described by way of examples which serve to illustrate the construction and testing of illustrative embodiments. However, it will be understood that the present invention is in no way limited to the examples set forth below.

EXAMPLES

The invention is illustrated by means of the following examples which in no case limit the scope of the invention.

Below there are several examples of the process developed for purifying levulinic acid from an aqueous phase comprising levulinic acid (LEVA) obtained from the hydrolysis of biomass. The methodology and experimental conditions applied in each example up to obtaining an aqueous phase comprising LEVA were the same for all the experiments described, being as follows.

Example 1. Production of an Aqueous Phase Enriched in Levulinic Acid

A biomass slurry formed by bleached lignocellulosic pulp in water was obtained by crushing, grinding, bleaching and dispersing lignocellulose biomass in a solution to create a slurry. The weight percentage of cellulose present in said biomass slurry was between 2.5 wt % and 9 wt % with respect to the total weight of the slurry. Said biomass slurry, with a ratio of liquid-solid of 3.5-10, was heated up to between 165-180° C. at a pressure of 7-10 barg in a hydrolysis reactor during between 0.5 and 4 h under stirring. Upon reaching said temperature and pressure values, sulfuric acid was injected until a sulfuric acid concentration of 2-4 wt % with respect to the total weight of the reaction mixture was reached. Then, the mixture was discharged and cooled down to room temperature. The solids were filtered off resulting in a liquid biomass hydrolysate (or liquor) comprising approximately 1.5-2 wt % levulinic acid (LEVA), 0.75-1 wt % of formic acid, and residues in water.

Therefore, the levulinic acid and formic acid yields were from 30% to 45% for levulinic acid, and from 15% to 22.5% for formic acid with respect to cellulosic fraction present in the biomass.

Example 1A: Purification Procedure a of Levulinic Acid by a Double Extraction Followed by a Distillation A first liquid-liquid extraction of LEVA from the aqueous solution (liquid biomass hydrolysate or liquor) was performed in an extraction column resulting in an organic solution comprising levulinic acid, and an aqueous solution. Methyl isobutyl ketone (MIBK) was used as organic solvent in a ratio of between 0.25:1 and 1:5 MIBK:liquor. The solvent and the liquor were fed to the extraction column at room temperature. After 12-2 extraction stages with contact times of 1-20 min an organic phase enriched in LEVA was collected. The efficiency of this extraction step was between 90%-98% for the levulinic acid and 90%-98% in the case of formic acid. Therefore, there was a 0.3-7.5 wt % of levulinic acid, a 0.15-4 wt % of formic acid in the obtained organic phase and between a 0.15 and 0.5 wt % of residues. Thus the ratio levulinic acid:residue was 1:0.6 in said organic phase.

The organic phase enriched in levulinic acid was then subjected to an aqueous liquid-liquid extraction by adding an aqueous solution (or fresh water) at a neutral pH to a mixer-settler equipment. The ratio of organic:aqueous phase was between 0.25:1 and 1:3 wherein the phases were mixed together under stirring (100-300 rpm) at room temperature (between 20 and 30° C.) and then, suffered a settling stage during 1-20 min that allows the phases to be separated by gravity resulting in an acidified aqueous phase comprising levulinic, formic and acetic acids among others.

Presence of humins and dissolved tar was indicated by the strong dark brown color of the residual organic phase (organic raffinate) which contained around an 80% or the initial colored lignin residues and humins. The efficiency of this aqueous extraction step was 95%-98% for the levulinic acid and 95%-98% in the case of formic acid. Therefore, the amount of levulinic acid in the aqueous solution obtained after the extraction step was 0.1-10 wt %, the amount of formic acid was 0.05-4 wt % and the amount of residues was about 0.06 wt %.

Thus, the stream comprising levulinic acid obtained after a double extraction (solvent extraction and aqueous extraction) had a ratio levulinic acid:residues of about 1:0.1 while the stream comprising levulinic acid after just one solvent extraction had a ratio levulinic acid:residue of about 1:0.6. Therefore, by performing an aqueous extraction a significant reduction of residues (around an 83% of residues reduction) in the stream comprising levulinic acid was observed.

Subsequently, the aqueous phase comprising levulinic acid was subjected to a distillation under vacuum. The distillation was performed at a pressure of 50-300 mbar with a bottom temperature of 30-70° C. Levulinic acid with a concentration between 90-95 wt % was recovered in the bottom remaining solution of the distillation. During the distillation, water and volatiles were collected in the distillate and were optionally recirculated into the aqueous liquid-liquid extraction step. Additionally, no dark-colored viscous residues were generated during the distillation step.

Example 1B: Purification Procedure B of Levulinic Acid by a Double Extraction Followed by a Nanofiltration and a Distillation The aqueous solution (liquid biomass hydrolysate or liquor) obtained in Example 1 followed the same procedure explained in example 1A for the purification of levulinic acid but including an additional step of a nanofiltration (membrane separation) after the aqueous liquid-liquid extraction step.

The aqueous solution obtained after the aqueous extraction step is separated (nanofiltrated) in a membrane unit. Transmembrane pressure is set on 20-40 bars and temperature kept at room T° C. The membrane is a DL Lenntech 150-300 Da. The permeate produced had a clear yellow color. The flux on average is between 40-60 $l/m^2 \cdot h$. The retentate obtained is diluted and optionally recirculated through the membrane. The calculated retention percentage (R), $R=(100(1-(C_{permeate}/Cr_{etentate})))$ for levulinic acid is around 15-25%. And the permeate percentage (P), $P=(100(C_{permeate}/Cr_{etentate}))$ for levulinic acid is 75-85%. A full retention of the humins and dissolved tar left in the aqueous solution was observed.

Subsequently, the aqueous phase obtained comprising levulinic acid as permeate was subjected to a distillation under vacuum as described in the previous example 1A. Levulinic acid with a concentration between 95-99 wt %, was recovered in the bottom remaining solution of the distillation.

Example 2: Comparative Example: Purification Procedure of Levulinic Acid by a Single Extraction (Solvent Extraction) Followed by a Distillation The aqueous solution obtained in the example 1 comprising approximately 1.5-2 wt % levulinic acid (LEVA), 0.75-1 wt % of formic acid, was purified as follows.

A liquid-liquid extraction of LEVA from the aqueous solution (liquid biomass hydrolysate or liquor) was performed in an extraction column resulting in an organic solution comprising levulinic acid, and an aqueous solution. Methyl isobutyl ketone (MIBK) was used as organic solvent in a ratio of 0.25:1 and 1:5 MIBK:liquor. The solvent and the liquor were fed to the extraction column at room temperature. After 12-2 extraction stages with contact times of 1-20 min an organic phase enriched in LEVA was collected. The efficiency of this extraction step was between 90%-98% for the levulinic acid and 90%-98% in the case of formic acid. Therefore, there was a 0.3-7.5 wt % of levulinic acid and a 0.15-4 wt % of formic acid in the obtained organic phase.

Subsequently, the organic phase comprising levulinic acid was subjected to a distillation. The distillation was performed at a pressure of 1 at. with a bottom temperature of 240-280° C. Levulinic acid with a concentration between 45-60 wt % was recovered in the bottom remaining distillation solution together with humins and tar residues among others. During the distillation, part of the solvent was collected in the distillate and was optionally recirculated into the liquid-liquid extraction step.

Subsequently, the bottom distillation solution comprising levulinic acid was subjected to a distillation under vacuum. The distillation was performed at a pressure of 10-15 mbar with a bottom temperature of 140-160° C. Levulinic acid with a concentration between 70-80 wt % was obtained in the distillate, the rest of the distillate comprises residues mostly lactones (between 10 and 20 wt %) and lignin residues (between 5 wt % and 10 wt %). The bottom remaining distillation solution was a viscous dark liquid comprising most of the lignin, humins and tar residues difficult of extract and manipulate.

By comparing the composition of the products obtained in examples 1A and 1B with the results obtained in the product of example 2 it was observed that the levulinic acid yield obtained by a double extraction followed by a distillation (example 1A) was higher than the one obtained for a single extraction followed by a distillation.

Example 3: Comparative Example: Purification Procedure of Levulinic Acid from an Organic Solution by Washing with a Basic Aqueous Solution (Process 3A) or Performing an Aqueous Extraction (Process 3B).

Two processes (named 3A and 3B) for purifying levulinic acid from an organic solution were compared. The initial organic solution comprised:
0.5 wt % of levulinic acid;
0.25 wt % of formic acid;
0.3 wt % of colored lignin residues;
0.08 wt % of other residues
in methyl isobutyl ketone (MIBK).

The ratio levulinic acid:residue in the final stream comprising levulinic acid was compared for 3A and 3B. It is worth noting that tar, colored lignin residues, char and other (humins) were considered residues.

Process 3A: Washing the Organic Solution with a Basic Aqueous Solution.

The organic solution described above was subjected to a washing step with a basic aqueous solution (pH 13.4 with NaOH) during 30 min under stirring at 60° C. The ratio of organic:aqueous phase used was 11:1. After a settling stage during 1-20 min, an organic phase was recovered comprising a ratio levulinic acid:colored lignin residue of around 6:1.

Process 3B: Extracting the Organic Solution with an Aqueous Solution.

The organic solution was subjected to an aqueous liquid-liquid extraction by adding an aqueous solution (or fresh water) at a neutral pH in a mixer-settler equipment. The ratio of organic:aqueous phase was 1:1. The phases were mixed together under stirring (100-300 rpm) at room temperature (between 20 and 30° C.) during 5 min and then, suffered a settling stage during 1-20 min that allows the phases to be separated by gravity. An acidified aqueous phase was obtained comprising a ratio levulinic acid:colored lignin residues of around 10:1. The aqueous extraction was also repeated with basic and acid solutions obtaining similar results than neutral solutions.

Then, the levulinic acid residue ratio obtained in 3A and in 3B showed that the purification by aqueous extraction was more effective than just washing the initial organic stream with a basic aqueous solution.

The invention claimed is:

1. A process for the purification of levulinic acid, comprising:
   i) providing an aqueous solution comprising levulinic acid;
   ii) subjecting the aqueous solution of step i) to an organic extraction to yield an organic solution and an aqueous solution;
   iii) subjecting the organic solution obtained in step ii) to an aqueous extraction to yield an aqueous solution, comprising levulinic acid, and an organic solution; and
   iv) subjecting the aqueous solution comprising levulinic acid obtained in step iii) to a membrane separation to yield an aqueous solution comprising levulinic acid, and a residue.

2. The process according to claim 1, further comprising:
   v) subjecting the aqueous solution comprising levulinic acid obtained in step iv) to at least one further purification step to yield an aqueous solution comprising levulinic acid.

3. The process according to claim 1, further comprising subjecting the aqueous solution comprising levulinic acid obtained in step iv) to a distillation to yield a distillate and a distillation solution comprising levulinic acid.

4. The process according to claim 1, wherein the aqueous solution provided in step i) or obtained in steps iii) or iv), the organic solution obtained in step ii), or any combination of them, are subjected to a partial evaporation step.

5. The process according to claim 1, wherein the aqueous solution comprising levulinic acid of step i) is obtained by
   i. providing a pulped lignocellulosic biomass;
   ii. optionally subjecting the pulped lignocellulosic biomass of step i) to a pre-hydrolysis to obtain a pre-hydrolyzed pulped lignocellulosic biomass;
   iii. subjecting the pulped lignocellulosic biomass provided in step i) or the pre-hydrolyzed pulped lignocellulosic biomass obtained in step ii) to an hydrolysis in the presence of an acid and under conditions of temperature, time, and acid concentration to yield an aqueous slurry comprising levulinic acid; and
   iv. subjecting the aqueous slurry comprising levulinic acid obtained in step iii) to a solid-liquid separation yielding to an aqueous solution comprising levulinic acid and a solid.

6. The process according to claim 1,
   wherein the organic extraction of step ii) is performed using a water-immiscible solvent selected from the group consisting of dicholoromethane (DCM), dichloroethene (DCE), 1,2-dichloroethane, toluene, benzene, 2-heptanone, butylacetate, methylisobutylketone (MIBK), dichloromethane, ethyl 5 propionate, 2-pentanone, diethyl ether, t-amyl alcohol, butanol, cyclohexanone, ethyl acetate, pyridine, tetrahydrofuran (THF), methyltetrahydrofuran (MTHF), 2-methyl tetrahydrofuran (2-ME-THF), 2-Butanone, acetone, dioxane, acetonitrile, formamide, N,N-dimethylformamide, dimethyl sulfoxide, ethylene glycol, methyl-ter-butylether (MTBE), cyclopentyl methylether (CPMe), heptane, dimethyl formamide (DMF), N-methylpyrrolidone (NMP), 2-sec-butylphenol (SBP), 4-npentylphenol (NPP), 4-n-hexylphenol (NHP) and diethyleneglycol dimethylether (DEGDME) and combinations thereof, and
   wherein the process further comprises forming a water-immiscible solvent:aqueous solution ratio between 0.25:1 and 4:1.

7. The process according to claim 1, wherein the organic extraction of step ii) or the aqueous extraction of step (iii) is performed using means able for extraction.

8. The process according to claim 1, wherein the organic extraction of step ii) or the aqueous extraction of step iii) are performed at room temperature.

9. The process according to claim 1, wherein the aqueous solution comprising levulinic acid obtained in steps iii) or iv) comprises at least a 0.1 wt % of levulinic acid.

10. The process according to claim 1 further comprising subjecting the aqueous solution comprising levulinic acid obtained in step iv) to a distillation to yield a distillate and a distillation solution comprising levulinic acid, wherein the distillation solution comprises at least 90 wt % of levulinic acid.

11. Process for the production of levulinic acid from pulped lignocellulosic biomass comprising the following steps:
(i) providing pulped lignocellulosic biomass;
(ii) optionally subjecting the pulped lignocellulosic biomass of step (i) to a pre-hydrolysis to obtain a pre-hydrolyzed pulped lignocellulosic biomass;
(iii) subjecting the pulped lignocellulosic biomass provided in step (i) or the pre-hydrolyzed pulped lignocellulosic biomass obtained in step (ii) to an hydrolysis in the presence of an acid and under conditions of temperature, time, and acid concentration to yield an aqueous slurry comprising levulinic acid;
(iv) subjecting the aqueous slurry obtained in step (iii) comprising levulinic acid to a solid-liquid separation yielding to an aqueous solution comprising levulinic acid and a solid;
(v) subjecting the aqueous solution obtained in step (iv) to an organic extraction to yield an organic solution and an aqueous solution;
(vi) subjecting the organic solution obtained in the previous step to an aqueous extraction to yield an aqueous solution, comprising levulinic acid, and an organic solution;
(vii) subjecting the aqueous solution comprising levulinic acid obtained in step (vi) to a membrane separation to yield an aqueous solution comprising levulinic acid, and a residue; and
(viii) optionally, subjecting the aqueous solution comprising levulinic acid obtained in the previous step to at least one further purification to yield an aqueous solution comprising levulinic acid.

12. The process according to claim 11, wherein the pulped lignocellulosic biomass of step (i) is obtained by:
a) providing biomass comprising a lignocellulosic material;
b) optionally, subjecting said biomass to a mechanical treatment; and
c) dispersing said biomass in a solvent to obtain pulped lignocellulosic biomass.

13. The process according to claim 11, wherein the aqueous solution comprising levulinic acid obtained in steps (vi), (vii) or (viii) comprises at least a 0.1 wt % of levulinic acid.

14. The process according to claim 11, wherein the aqueous solution obtained in steps (iv), (vi), (vii) or (viii), the organic solution obtained in step (v), or any combination of them, are subjected to a partial evaporation step.

15. The process according to claim 11, further comprising subjecting the aqueous solution comprising levulinic acid obtained in steps (vii) or (viii) to a distillation to yield a distillate and a distillation solution comprising levulinic acid; wherein the distillation solution comprises at least 90 wt % of levulinic acid.

16. The process according to claim 1, further comprising:
v) subjecting the aqueous solution comprising levulinic acid obtained in step iv) to at least one further purification step to yield an aqueous solution comprising levulinic acid; and
vi) subjecting the aqueous solution comprising levulinic acid obtained in step v) to a distillation to yield a distillate and a distillation solution comprising levulinic acid.

17. The process according to claim 1, further comprising:
v) subjecting the aqueous solution comprising levulinic acid obtained in step iv) to at least one further purification step to yield an aqueous solution comprising levulinic acid,
wherein the aqueous solution obtained in step v) is subjected to a partial evaporation step.

18. The process according to claim 1, further comprising:
v) subjecting the aqueous solution comprising levulinic acid obtained in step iv) to at least one further purification step to yield an aqueous solution comprising at least a 0.1 wt % of levulinic acid.

19. The process according to claim 1, further comprising:
v) subjecting the aqueous solution comprising levulinic acid obtained in step iv) to at least one further purification step to yield an aqueous solution comprising levulinic acid; and
vi) subjecting the aqueous solution comprising levulinic acid obtained in step v) to a distillation to yield a distillate and a distillation solution comprising at least 90 wt % of levulinic acid.

* * * * *